United States Patent [19]
Carpentier et al.

[11] Patent Number: 5,972,020
[45] Date of Patent: *Oct. 26, 1999

[54] SURGICAL INSTRUMENT FOR CARDIAC VALVE REPAIR ON THE BEATING HEART

[75] Inventors: Alain Carpentier, Paris, France; Charles S. Taylor, San Francisco, Calif.

[73] Assignee: Cardiothoracic Systems, Inc., Cupertino, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/801,129

[22] Filed: Feb. 14, 1997

[51] Int. Cl.⁶ .................................................. A61B 17/28
[52] U.S. Cl. ...................... 606/208; 600/114; 604/256; 294/104
[58] Field of Search .................................. 606/208, 151, 606/108, 154, 1, 205, 207, 51–52; 604/264, 167, 116, 256; 600/21, 22, 114, 121–125, 205, 218; 294/103.1, 104; 632/2

[56] References Cited

U.S. PATENT DOCUMENTS

| | | |
|---|---|---|
| 396,754 | 1/1889 | Mayfield . |
| 4,023,559 | 5/1977 | Gaskell .................................. 604/280 |
| 4,240,411 | 12/1980 | Hosono .................................. 604/167 |
| 4,735,606 | 4/1988 | Davison . |
| 4,850,969 | 7/1989 | Jackson .................................... 604/96 |
| 5,057,098 | 10/1991 | Zelman . |
| 5,139,478 | 8/1992 | Koninckx et al. ........................ 604/26 |
| 5,217,458 | 6/1993 | Parins . |
| 5,246,419 | 9/1993 | Absten .................................... 604/26 |
| 5,374,254 | 12/1994 | Buma . |
| 5,797,888 | 8/1998 | Yoon . |
| 5,797,931 | 8/1998 | Bito el al. . |

FOREIGN PATENT DOCUMENTS

94/11052  5/1994  WIPO .
WO96/32882  10/1996  WIPO .

*Primary Examiner*—Mark Bockelman
*Attorney, Agent, or Firm*—Lyon & Lyon LLP

[57] ABSTRACT

The invention is an apparatus and method to perform a surgical procedure within the beating heart. The instrument provides a seal to surround cardiac tissue, thereby defining a segregated surgical field within the body of the instrument. A suction device is preferred to remove blood and fluids from the surgical field so that a surgical procedure can be performed while the heart continues to beat. The instrument is particularly suitable for a procedure to repair defective or diseased cardiac valves, such as the mitral valve; a procedure which previously required that the heart be stopped so that the corrective surgical procedure could be performed.

32 Claims, 6 Drawing Sheets

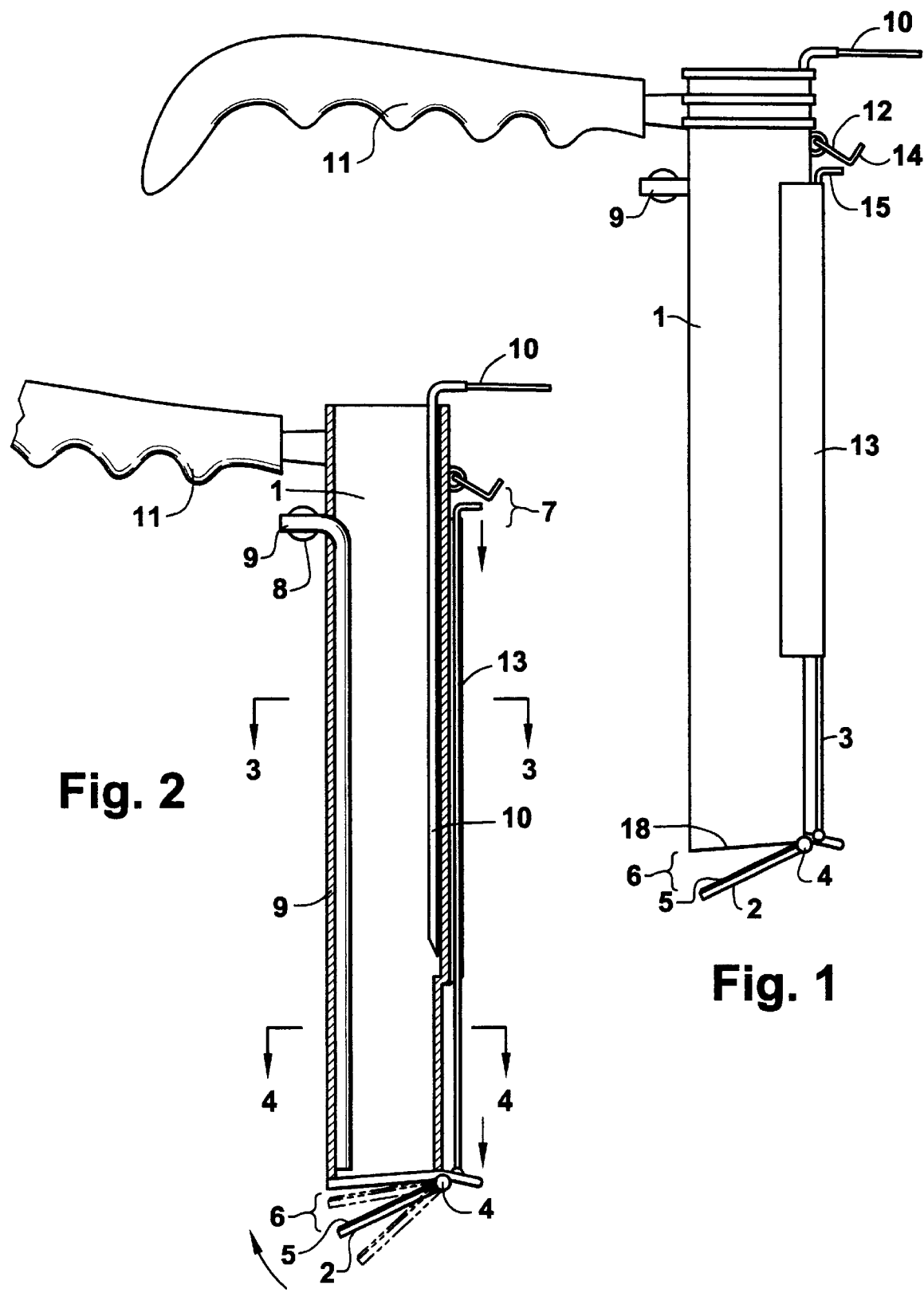

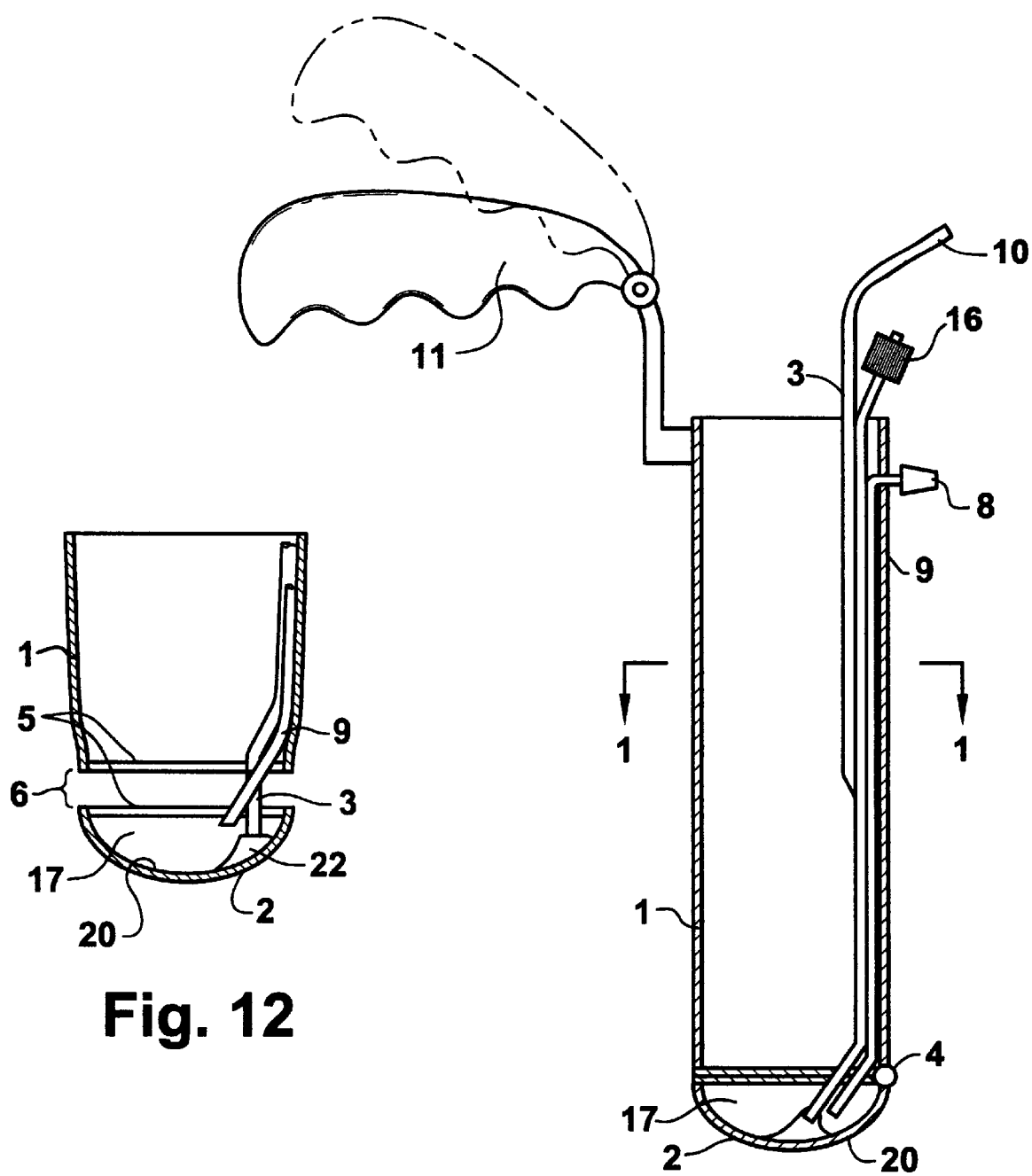

SURGICAL INSTRUMENT FOR CARDIAC VALVE REPAIR ON THE BEATING HEART

FIELD OF THE INVENTION

The invention relates to the field of surgical instruments which are specially designed to facilitate surgery on the interior structures of the beating heart, in particular, the valves.

BACKGROUND OF THE INVENTION

For several decades, surgeons have been performing a wide variety of surgical procedures on the heart. The advent of cardiopulmonary bypass (CPB) allowed surgeons to stop the heart while maintaining a flow of oxygenated blood throughout the rest of the body such that lengthy and highly invasive surgical procedures on the heart could be performed. The CPB apparatus and procedure enabled more widespread practice of cardiac surgery by allowing surgeons to temporarily isolate the heart from the circulatory pathway while extensive and complex repair and reconstruction procedures were performed on the muscles, valves, arteries, etc. of the heart while the heart itself remained static. Although CPB provides the surgeon with the ability to perform certain procedures, connecting the patient to the CPB apparatus is time consuming and traumatic to the patient. In establishing CPB by traditional techniques, the chest is opened by cutting through the sternum and spreading the ribs, large bore cannulas are placed in the patient's venous and arterial system, the heart is stopped by infusion of chemicals, the aorta which supplies blood to the body from the heart is clamped shut, thus separating the heart from the rest of the circulatory system, and the patient's blood supply is circulated outside the body through a mechanical pump and a device to oxygenate the blood.

The CPB procedure has several well-known drawbacks and new information regarding the adverse effects of CPB is continually being discovered. For example, CPB runs the risk of causing ischemic/reperfusion injury in the heart and elsewhere in the body where blood flow is reduced or interrupted and restarted. The problem is particularly significant in the brain where peri-operative strokes and related neurological disorders have been observed in patients following CPB which may result from particles which cause interruptions in the blood supply to the brain. Also, the heart may sustain damage from the CPB process or from the CPB apparatus which results in reduced blood pumping capacity and other irregularities. Furthermore, damage to the blood itself results from passing the blood through the CPB pump and from surface interactions between the patient's blood and the synthetic surfaces inside the pump and associated apparatus. Due to the adverse effects of CPB, surgeons attempt to limit the amount of time that the patient is subjected to CPB and prefer to avoid CPB whenever possible.

Recently, to avoid the need for CPB, techniques and apparatus have been developed to enable surgeons to perform certain types of cardiac surgeries on the beating heart. Principal among these is coronary artery bypass graft surgery (CABG) wherein an obstructed coronary artery, which tends to be located at or near the surface of the exterior of the heart, is bypassed with another source artery or a graft to restore blood flow to the muscles of the heart beyond the obstruction. The prime rationale for the development of the beating-heart procedures is to avoid CPB, and surgeons and engineers are constantly searching for techniques and apparatus to expand the repertoire of beating-heart surgical procedures.

For surgical procedures involving structures and chambers internal to the heart, there is another important rationale for using a beating-heart approach. Many of these procedures require maintaining an opening through the epicardial and myocardial tissue to expose and allow access to the internal target area. An unavoidable result is the introduction of air into the chambers which must be removed to minimize the risk of air bubbles which can lead to stroke. The removal of air in these conventional procedures is accomplished after correcting the defect but prior to resuming normal heart-lung function by closing all myocardial incisions with the exception of a small opening or vent hole and massaging the heart to cause any entrapped air to escape through the opening. The opening is then sutured closed. This technique can be traumatic and damaging to the myocardium and the chambers, and especially to the newly treated target area. Moreover, there is no way of guaranteeing that all air is removed from the heart. Conversely, with a beating-heart approach, the introduction of air could be minimized as atmospheric exposure of the internal chambers must be limited to prevent the loss of blood. In addition, the patient's blood pressure would act to minimize the introduction of any air. Therefore, a need exists for instrumentation that would enable a beating-heart approach to surgical repair of internal cardiac structures while minimizing the risk of air entering the patient's circulatory system.

Surgical procedures involving the repair of structures inside the beating heart, such as the cardiac valves which control and regulate blood flow into, out of, and between the four chambers of the heart, the left and right atria and the left and right ventricles, are very difficult to perform. A surgical procedure on a heart valve is particularly difficult to perform on a beating heart because the valves are located inside the heart and continuously open and close to regulate the flow of blood. Moreover, the valves are immediately proximate to the atria and ventricles which continuously contract to cause blood to flow from the venous system, to the lungs to be oxygenated, and then throughout the body. Still further, the valves must control a volume of blood which may be under considerable pressure due to the contraction of the muscles of the heart. As such, it is extremely difficult to provide a bloodless field within which the surgeon has adequate visibility of the surgical area. Moreover, the continual opening and closing of a valve makes it difficult to perform delicate surgical tasks, such as suturing, which require a high degree of accuracy and precision.

Valve surgery on the beating heart is rendered even more problematic due to the substantial absence of special tools to enable surgical operations inside the beating heart. Among the difficulties inherent in beating heart valvular surgery are the need to work in a moving field, the need to prevent the flow of blood from obstructing the surgical field, and in the case of valvular surgery, the need to isolate a portion of the valve being repaired from the blood flow which is continuing in the remainder of the beating heart, and the need to allow the valves to continue to perform substantially their normal functions during the surgery. Thus, there is a substantial need for instrumentation and new surgical techniques for addressing these difficulties.

SUMMARY OF THE INVENTION

This invention includes specially designed instruments and methods for performing cardiac surgery on structures inside the heart while the heart continues to beat. The instrument provides the capability to isolate and substantially immobilize a portion of the internal cardiac tissue, such as the leaflet of a valve, while simultaneously providing an unobstructed and segregated surgical field in which the surgeon may operate to perform a surgical procedure.

Generally, the structure of the instrument is comprised of a body having a sealable portion of which all or a portion thereof is inserted into the beating heart to define a surgical field inside the beating heart and which isolates the surgical field from the blood flow. The segregated surgical field may be substantially contained within the interior of the beating heart and is defined by the design and structure of the instrument. The body of the instrument also has a sealable opening, preferably at a distal end, such that structures on the interior of the heart can be introduced through the opening and into the segregated surgical field within the beating heart. A movable sealing member conforms to the body of the instrument to provide a conformable gasket-like sealing means which provides a fluid impermeable seal between the interior of the beating heart and the segregated surgical field when a sealable opening therein is closed. The particular target structure of the heart on which the surgical procedure is to be performed, such as a valve leaflet, is introduced to the surgical field through the sealable opening in the body of the instrument. Substantially closing the sealable opening about the target structure creates a segregated surgical field where the target structure is inside the instrument and may be accessed by the surgeon. The instrument is used with, and may integrally contain, a vacuum suction aspirator or other device to evacuate blood and other fluids from the interior of the body of the instrument and the segregated surgical field once the sealable opening in the instrument is closed about the target cardiac structure. Once the surgical field is clear, the surgeon introduces additional surgical apparatus and instruments through the body of the instrument to perform the desired operation while the heart continues to beat.

DESCRIPTION OF THE FIGURES

FIG. 1 is the exterior of an embodiment of the invention which includes a substantially cylindrical body, a substantially planar sealing member, means for actuating and fixing the position of the sealing member, a handle for positioning the instrument and a light source and a vacuum aspirator introduced through the proximal end thereof.

FIG. 2 is a cross-section of the embodiment of FIG. 1 revealing the interior of the instrument of the invention and one possible configuration of a light source and vacuum aspirator located inside the body of the instrument.

FIG. 10 is an additional embodiment of the invention having a movable handle and a configuration for the sealing member such that the entire structure thereof is displaced beneath the body of the instrument, and wherein a vacuum aspirator extends into the extended surgical field to remove fluids therefrom.

FIG. 11 is a cross-section of the embodiment of FIG. 10 showing one internal configuration for the vacuum aspirator, the light source, and an adjustable means for positioning the sealing member.

FIG. 12 is an isolated view of another configuration of the distal portion of the invention, showing an alternative closing mechanism for the sealing member.

DETAILED DESCRIPTION OF THE INVENTION

Figure 3:
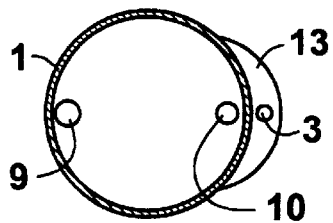
FIG. 3 is a cross-section about line 3—3 in FIG. 2 above, revealing an interior configuration for the light source and vacuum aspirator.

The following description may refer in particular to a procedure or a configuration of the apparatus particularly suited to valvular surgery, and may refer to valve surgery by example. However, the invention is also applicable to other structures and surgical procedures internal of the beating heart. The body of the instrument of the invention may take several different shapes, preferably however, the body is substantially cylindrical having the sealable opening at the bottom (distal) end thereof where the segregated surgical field is created by the sealing member engaging the lower end of the substantially cylindrical body enabling thereby the sealable opening to be brought into proximity with the region of the cardiac tissue proximate to the site of the surgery. The (distal) lower end of the body of the instrument provides a substantially sealed portion comprised of a sealable opening and a gasket-like sealing member to create the segregated surgical field internal to the beating heart. The upper (proximal) end of the body of one embodiment of the instrument is open such that surgical instruments and related apparatus are introduced to the segregated surgical field through the body of the instrument of the invention. Alternately, the upper portion of the body may be closed and have sealable ports therein for delivery of surgical instruments to the segregated surgical field.

The insertion of the device through the epicardial layers of the heart may be achieved through a sealable incision provided with a purse-string suture or suture cuff installed in the pericardium and myocardium. An incision is made of sufficient length to insert the sealed portion of the body of the instrument through the myocardium. Once inserted, the tissue surrounding the incision is quickly sealed around the outside of the body of the instrument, for example by the purse string, to prevent excessive loss of blood. Once the incision is sealed around the outside of the body of the instrument, the distal end of the instrument may be oriented to bring the sealable opening to the specific site of the surgery.

The sealable opening may be provided by a trap-like sealing member which seals against the body of the instrument when the sealable opening is substantially closed and which forms a seal with the body of the instrument and thereby surrounding the cardiac tissue proximate to the region where the procedure is to be performed. The positioning of the cardiac tissue within the segregated surgical field defined by the instrument may also be facilitated by passing a suture through the cardiac tissue and then drawing the suture through the body of the instrument and through the open end at the proximal end of the instrument. By exerting tension on the suture line, the tissue is more readily oriented into the sealable opening of the instrument, and thereby, into the segregated surgical field. Thus, by manipulation of the tissue and the instrument itself, a portion of cardiac tissue, such as a portion of a valve, may be introduced to the interior of the body of the instrument through the sealable opening and is maintained in a segregated surgical field.

By bringing the sealing member into close conformity with the body of the instrument, the sealable opening is substantially closed and a portion of cardiac tissue, such as the leaflet of a valve, is then isolated within the segregated surgical field and the segregated surgical field is in fluid isolation from the remainder of the beating heart. Substantial closure of the sealable opening followed by evacuation of fluids creates an unobstructed and segregated surgical field within the body of the instrument. The closure or sealing of the sealable member to the body of the instrument is said to be "substantial" because cardiac tissue may be disposed within the sealable opening and may provide a portion of the overall sealing function. An aspirator or equivalent suction or blower device may be introduced into the interior of the body of the instrument to keep the surgical field clear of fluids and may also contain other conventional surgical apparatus such as irrigators, lights, stitchers, clamps, suture needles, cameras, etc. If desired, the associated surgical apparatus such as aspirators and light sources may be integrally associated with the body of the instrument.

As noted above, the body of the instrument may be substantially cylindrical and may be a unitary structure or may be comprised of independent sections which are added or removed based on the clinical circumstances attendant to the surgery. For example, in a procedure where the sealable opening is positioned within the heart in a region with a volume of blood under high pressure, blood may rapidly fill the interior of the body of the instrument and can overflow. In such circumstances, the body of the instrument may have an extension which preferably attaches to the proximal end to increase the internal volume of the instrument and to permit containment of a larger volume of blood. The depth of the instrument and the resulting pressure head developed balance the pressure of blood within the cardiac chamber into which the instrument has been inserted. Depending on the type of surgical procedure, the targeted surgical structure, the size of the heart chamber being worked on, and the anatomy of the particular patient, the volume of the instrument of the present invention is chosen to accommodate a requisite depth of blood to minimize the risk of overflow.

Alternately, the body of the instrument may have a covered or closed proximal end whereby the risk of overflow is obviated. In this embodiment, small sealable ports or holes are provided through the closed proximal end for delivery of surgical tools, scopes, clear fluid, and the like.

In the mitral valve surgery example, the instrument is inserted through the exterior of the heart to be brought into proximity with the site of the surgery at the interior of the heart, such as the mitral valve, where the surgeon will often repair damage to the individual leaflets which form the valve. By manipulating the instrument of the invention, the surgeon may introduce the leaflet into the sealable opening of the instrument and bring the sealable member into a position which conforms the sealable member with the body of the instrument such that the opening is sealed and the valve leaflet is positioned within the segregated surgical field. In such a configuration, the remaining leaflets of the valve will abut the exterior of the sealed portion of the body of the instrument while the heart continues to beat. Depending on the location of the surgery within the beating heart, the exterior of the heart, i.e., the pericardium and myocardium, may be closed around the exterior of the body of the instrument, such as by a clamp or purse-string suture, to avoid blood loss and the introduction of air into the patient's circulatory system. The surgeon can freely position the instrument by manipulating a handle which is preferably affixed to an upper (proximal) portion of the body of the instrument.

As noted, the use of the device is advantageous in that an unobstructed and segregated surgical field is defined inside the beating heart. This field may be separately irrigated, ventilated, or exposed to other chemical or physical agents, manipulations or treatments, separate from the remainder of the heart and separate from the circulatory pathway for the remainder of the body. If the access to the beating heart is provided by a less invasive procedure, i.e., a mini-thoracotomy rather than traditional "open heart" techniques, the body of the instrument should have a length sufficient to introduce the sealed portion of the body of the instrument to the interior of the beating heart by passing between the ribs and through the closed chest cavity. In this case, the instrument preferably has a substantially cylindrical body of a sufficient length to reach all of the internal structures of the heart while the positioning of the device is achieved by manipulating the handle from outside the chest cavity. In such a configuration, the sealed portion of the instrument may be the entire length of the body of the instrument which is inserted into the chest cavity. In each embodiment, all exterior surfaces of the instrument are preferably smooth to avoid damage to the heart and surrounding tissues when the instrument is inserted and removed.

Once the instrument of the invention is in proximity to the site of the surgery, the cardiac tissue is introduced through the sealable opening as described above and the sealable opening is effectively sealed by manipulating the sealing member into an orientation necessary to prevent the flow of blood into the segregated surgical field. The sealing member can be provided in several shapes, depending on the shape of the body of the instrument, and can be oriented by remote manipulation. In one embodiment, the sealing member is a substantially planar "trap"-like structure positioned at the most distal portion of the body of the instrument. The sealing member may move independently of the body of the instrument or may move about a pivot located at one edge of the periphery of the circumference of the body of the instrument. A means for positioning the sealing member is provided, for example, by a vertical rod which has one end affixed to the sealing member appositive the pivot. The sealing member may be actuated by vertical movement of a rod or shaft. By moving the shaft upward, the sealing means contacts the tissue disposed within the opening and forms a seal surrounding the tissue to prevent fluid from entering the segregated surgical field within the sealed portion of the body of the instrument. Once the sealing member is properly positioned, the sealing member can be fixed in place by a locking mechanism, thumbnut, or other such conventional mechanism.

The seal between the sealing member and the body of the instrument is provided by a soft conformable material which covers all or substantially all of the entire area of contact between the sealable member and the body of the instrument. For example, with a cylindrical embodiment, the conformable material covers the annular edge at the bottom of the sealed portion of the body of the instrument and the annular edge of the sealing member such that when the sealing member is brought in proximity with the body of the instrument, with a portion of tissue disposed therebetween, the sealable opening is substantially closed and the conformable material contacts both of the upper and lower surfaces of the tissue to form a fluid impervious seal between the interior of the instrument and the interior of the beating heart. At any space where tissue is not disposed therebetween, the conformable material of the sealed portion of the body and the sealing member respectively are in direct contact with each other to provide the complete seal required to keep fluid from entering the segregated surgical field.

The precise dimensions of the instrument may be varied depending on the particular design and application of the instrument. Preferably, the instrument has a height of approximately 90 mm (3.5 inches) or less, has an external diameter of approximately 30 mm (1.2 inches) at the distal end and approximately 40 mm (1.6 inches) at the proximal end. The inner diameter of the body 1 of the instrument may be approximately 27 mm (1 inch).

Referring now to the drawings, wherein like reference numbers indicated like elements, and in particular to the embodiment of the invention of FIG. 1, the body of the instrument 1 is sealed along its entire length and has a movable sealing member 2 at the distal end of the body 1. Movement of a sealing member 2 is achieved by manipulation of a means for positioning the sealing member comprising a movable rod 3 which, in this example, orients the sealing member 2 about a pivot 4 affixed to the periphery of the distal end of the body 1 of the instrument. The angle created between sealing member 2 and the edge 18 of the distal end of the body of instrument 1 may be approximately 35° when sealing member 2 is in an open position, but may be more or less depending on the dimensions of the target cardiac tissue. The size or angle of sealable opening 6 need only be large enough to accommodate the target cardiac tissue therein. The side of edge 18 opposite pivot 4 is angled slightly downward from the body to maximize the draining of blood via fluid communication port 9.

The upper surface of the sealing member 2, which abuts the body 1 of the instrument and which contacts the cardiac tissue, has a conformable sealing means 5 placed about the periphery thereof. Conformable sealing means 5 may cover the entire upper surface of the sealing member 2 or may cover a substantial portion of the periphery thereof. Conformable sealing means 5 may have a uniform thickness or may be tapered along its length to achieve the best seal when sealing member 2 is closed.

The proximal end of the instrument may have a handle 11 which may be permanently attached to the body 1 of the instrument or may be removable. Handle 11 is preferably rotatable about the body 1 of the instrument and is shaped to be held by the hand. For maximum freedom of movement, handle 11 may be rotatable about the complete axis of the body 1 of the instrument. Handle 11 is used to position the instrument when it is introduced to the beating heart, i.e., through a sternotomy or thoracotomy, and particularly when the instrument is introduced to the interior of the beating heart.

Referring to FIG. 2, one possible arrangement for certain elements of the device of the invention is shown in a cross-sectional view of the device. In this embodiment, the means for positioning the sealing member, such as movable rod 3 is substantially external to the body of the instrument as shown in FIG. 1. The movable rod 3 may be contained within a separate housing 13 mounted on the exterior of the body 1 of the instrument or may run through the interior of the body 1 of the instrument (not shown) and still be affixed to the sealing member 2. The uppermost end of the movable rod 3 may have a locking mechanism 7 to fix the position of the movable rod 3 so that the position of the sealing member 2 relative to the body 1 of the instrument can be fixed when the sealable opening 6 is substantially closed.

The locking mechanisms of FIGS. 1 and 2 may be an elbow 15 at the uppermost portion of the movable rod 3 which abuts a latch 12 which has a flat section 14 shaped to contact the elbow 15 at the uppermost portion of the movable rod 3. Several alternative mechanical designs for the locking mechanism may be readily provided. For example, a thumb screw or nut at the uppermost portion of the movable rod 3 allows continuous lockable positioning of the movable rod 3 and continuous positioning of the sealing member 2 (See FIGS. 7 and 10).

The embodiment of FIG. 2 has a fluid evacuation means 8 comprising a vacuum aspirator integrally associated with the body 1 of the instrument and having an air communication pathway 9 running from the upper portion of the body 1 of the instrument to the distal end adjacent the sealable opening 6. The fluid evacuation means 8 need not be integral with the body of the instrument and may be provided during the surgical procedure by a conventional suction apparatus. However, it is preferred that the fluid evacuation means 8 be continuously operated within the instrument during the procedure so that fluids can be continuously removed from the segregated surgical field. The interior of the body 1 of the instrument may also be provided with a light source and/or an endoscope 10 to illuminate and provide viewing of the segregated surgical field. As with the fluid evacuation means 8, the light source or scope 10 may be integral to the body 1 of the instrument or may be separately introduced through the body 1 of the instrument through the open end.

FIG. 3 is a cross-section through line 3—3 of FIG. 2 showing the internal space of the body 1 of the invention and one configuration for the air communication pathway 9, light source and/or scope 10, and movable rod 3. In this embodiment, the movable rod 3 is partially contained within a separate housing 13.

Figure 4:
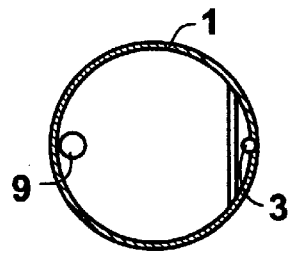
FIG. 4 is a cross-section view of FIG. 2 above, showing the means for actuating and fixing the position of the sealing member passing outside the substantially cylindrical body of the device of the invention.

FIG. 4 is a cross-section of the embodiment of FIG. 2 through line 4—4 showing a configuration of the interior of the body of the invention at a more distal portion thereof. At the more distal portion, the movable rod is outside the body 1 having extended beyond the separate housing 13.

Figure 5:
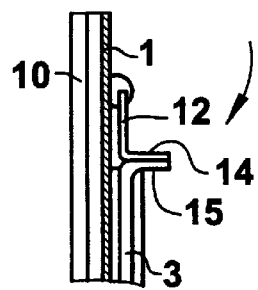
FIG. 5 is a close-up view of one configuration for a locking mechanism to fix the position of the sealing member in close engagement with the distal end, the body of the instrument.

FIG. 5 is an isolated view of the movable rod locking mechanism at the proximal portion of the invention. To lock the movable rod 3 in place, latch 12 is positioned such that a flat section 14 contacts an elbow 15 at the upper-most (most proximal) portion of the movable rod 3. By bringing the flat section 14 of latch 12 and the elbow 15 into a locking relationship, as shown in FIG. 5, the position of the movable rod 3 is fixed, thereby fixing the position of the sealing member 2 relative to the body of the housing 1 by setting the downward position of movable rod 3 about pivot 4.

Figure 6:
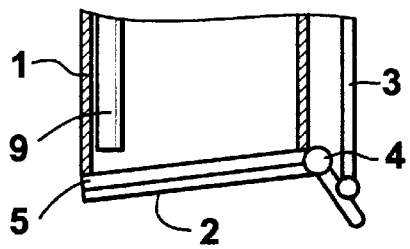
FIG. 6 is a close-up view of the sealing member in the closed position to provide a fluid-impermeable seal at the distal end of the instrument.

Thus, as shown in FIG. 6, when the movable rod 3 is fixed in the most downward position, the sealing member 2 closes sealable opening 6 by engaging the distal portion of housing 1. In this embodiment, the conformable sealing means 5 is affixed at least to the upper-most (proximal) portion of sealing member 2 and may also be affixed to the bottom surface of the distal portion of the body 1.

Figure 7:
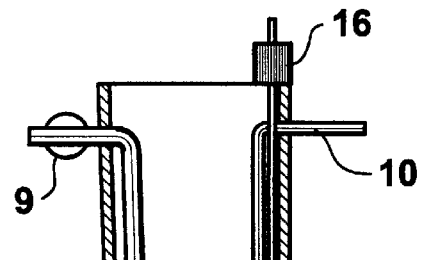
FIG. 7 is a schematic outline of an additional embodiment of the instrument of the invention having a concave sealing member which provides an enlarged surgical field within the body of the instrument by extending the surgical field beneath the level of the sealed opening.

FIG. 7 illustrates an additional configuration of one embodiment of the invention. The sealing member 2 in this embodiment is non-planar and may be concave at the interior surface 20 to provide an enlarged internal volume 17 for the segregated surgical field inside the body 1 of the instrument. This configuration provides the surgeon with the advantage of an extended segregated surgical field 17 and a working space below the level of the sealable opening 6 and, hence, below the level of the tissue positioned therein.

As with the embodiment of FIG. 2, this embodiment of the device of the invention is provided with a fluid evacuation means 8, which is generally comprised of an air communication pathway 9 running from the upper portion of the body 1 to the distal end adjacent the sealable opening 6. A light and/or viewing source 10 is also provided to illuminate and facilitate viewing of segregated surgical field 17. In this embodiment, the movable shaft 3 is contained entirely within the body 1 of the instrument and is attached to the sealing member 2 at a point within the extended surgical field 17. Various configurations for this attachment are contemplated, and include, for example, a link or loop-like protrusion 19 extending from surface 20 which can be grasped or engaged by a hooked or bent distal end 21 of rod 3. As mentioned above, the positioning of the movable shaft 3 may be adjusted by a thumb screw 16 located at the proximal end of the body 1 of the instrument.

Figure 8:
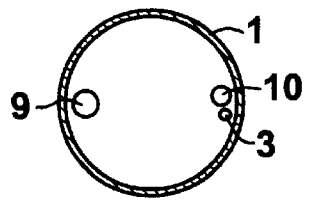
FIG. 8 is a cross-section of the embodiment of FIG. 7, showing one internal configuration for the light source, vacuum aspirator, and a means for adjustable positioning of the sealing member.

Referring to FIG. 8. a cross-section of the embodiment of FIG. 7 is shown about line 8—8. The internal configuration of this embodiment is similar to that described previously, and has an air communication pathway 9 and a light source and/or viewing means 10 disposed therein. Note that the movable rod 3 is also located within the body 1 of the instrument.

Figure 9:
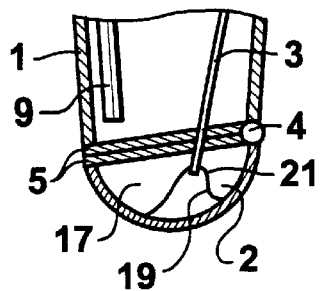
FIG. 9 is an isolated view of the distal portion of the embodiment of FIG. 7, showing the extended surgical field beneath the level of the sealed opening.

In FIG. 9, an isolated view of the most distal portion of the embodiment of FIG. 7 is shown in a position where the sealable member 2 is closed. Thus, an extended surgical field 17 is provided below the level of the sealable opening 6. In this configuration, the conformable sealing means 5 is attached to both the upper (proximal) portion of sealing member 2 and the lower (distal) portion of the body 1.

Referring to FIG. 10, an additional configuration of the device of the invention is shown, having a movable handle 11 which can be lifted upwards (as shown in phantom) to accommodate positioning of instrument 1 at any depth when operably positioned within the chest cavity. As with the embodiments of FIGS. 2 and 7, this configuration also provides a fluid communication pathway 9. However, in this embodiment, air communication pathway 9 terminates at a lever below the level of the sealable opening to provide a bloodless field below the level of tissue when positioned within surgical field 17. FIG. 11 shows a cross-section through line 11—11 of FIG. 10, revealing the internal configuration of the embodiment of FIG. 10 wherein the scope means and/or light source 10, movable shaft 3, and air communication pathway 9 are placed in close proximity to one another to be as unobtrusive as possible during the surgery. The sealing member 2 has a configuration similar to that of FIG. 7.

Referring to FIG. 12, another embodiment is shown wherein the sealable opening 6 is created such that the upper portion of the sealing member 2 and the lower portion of the body 1 are substantially parallel to each other when sealing member 2 is in an open position. As in the above embodiments, positioning of the sealing member 2 by a movable rod 3 seals the sealing member 2 against the body 1 at conformable sealing means 5 to close and seal the sealable opening 6. However, in lieu of a hinged sealing member and a hooked rod and loop configuration, rod 3 of FIG. 12 is affixed to interior surface 20 by means, for example, of a solder connection 22 or other like means.

Figure 16:
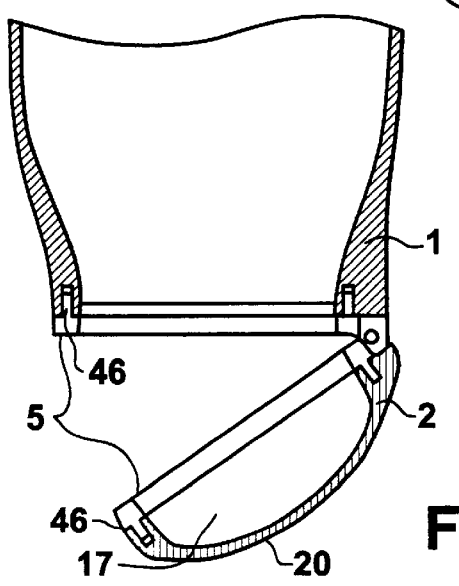
FIG. 16 is an isolated view of one configuration of the distal portion of the invention, and in particular, a configuration for the sealing member.

An enlarged detailed view of one embodiment of the sealing member 2 and associated sealing means 5 of the present invention is shown in FIG. 16. Sealing means 5 is in the form of dual annular elements which are held within annular retaining grooves 46. Sealing means 5 is made of highly compressible material such as silicone or other elastomer so as to be easily conformable to cardiac tissue around which it seals.

Figure 13:
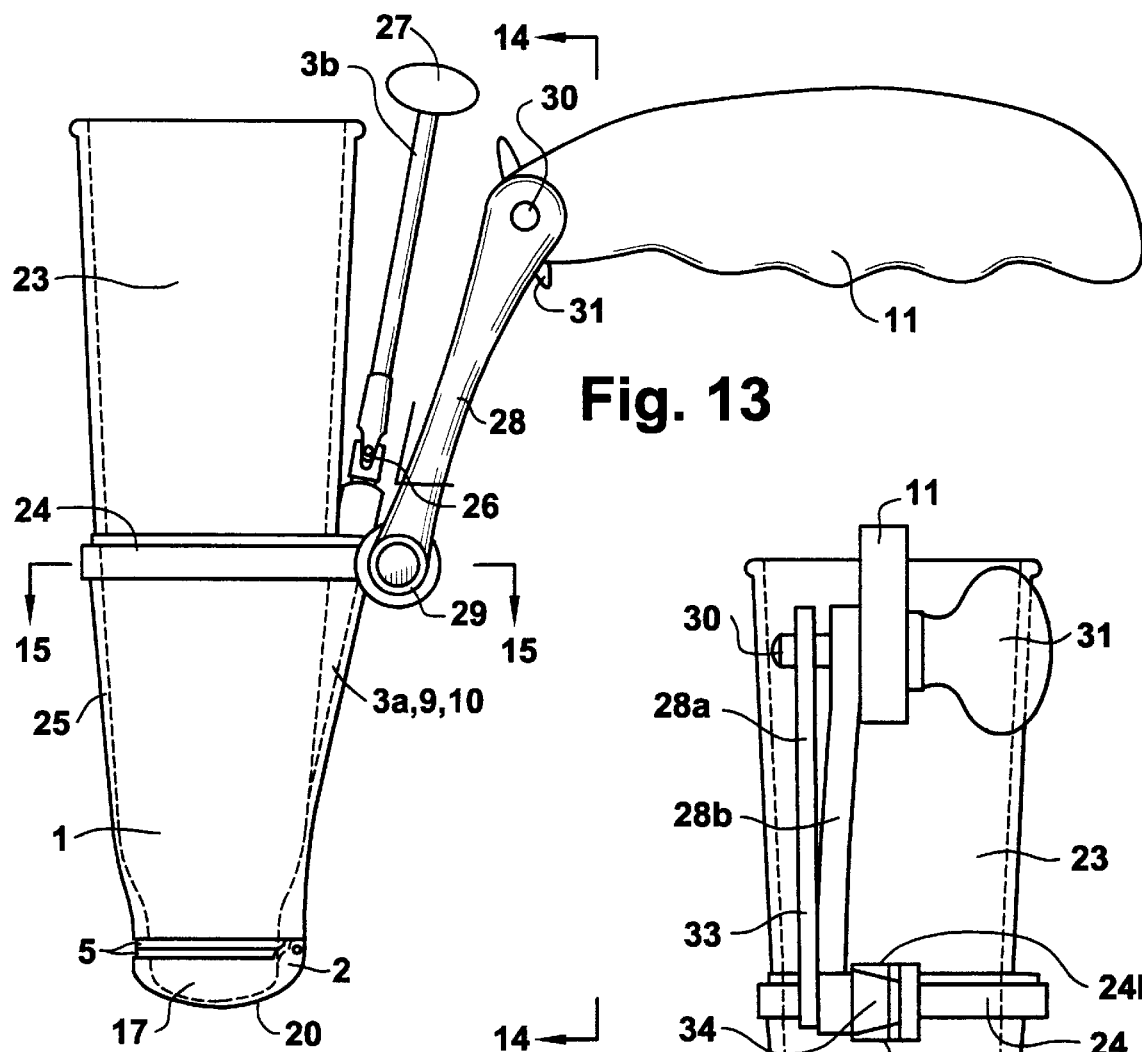
FIG. 13 is a preferred configuration for the body of the instrument having the detachable upper section affixed to the proximal end of the instrument to expand the internal volume of the body of the instrument, and also having an alternate handle configuration.

Referring now to FIG. 13, there is shown a preferred embodiment of the invention having a detachable upper section 23 which is sealingly engaged within the proximal end of body 1, by means of an "o-ring" (not shown) positioned around the external diameter of the distal end of upper section 23. This combined structure provides an expanded internal volume and height approximately double that of body 1 alone. Such an expanded internal volume provides containment of a larger volume of blood and prevents overflow during a beating-heart procedure. After blood has been removed by aspiration via fluid communication port 9, detachable upper section 23 may be manually detached by an upward pulling or twisting motion. As such, the height or length of the instrument 1 is reduced by approximately half, facilitating the surgeon's access to and the delivery of surgical tools to the surgical area.

Figure 15:
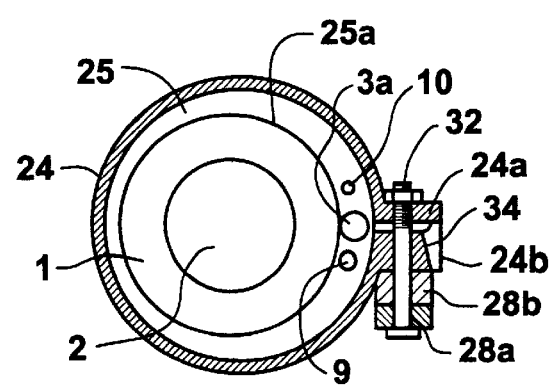
FIG. 15 is a cross-section of the embodiment of FIG. 13 through line 15—15 showing the extended diameter section of the embodiment.

Upper section 23 and body 1 have substantially conical shapes, having diameters which narrow gradually, proximally to distally, with the distal end of upper section 23 having an outer diameter which allows it to be positioned within the proximal end of body 1. As is more clearly shown in FIG. 15, which provides a cross-sectional view of FIG. 13 along line 15—15, the outer wall 25 of body 1 has a thicker portion 25a for accommodating various ports such as for a moveable rod 3a (shown partially in phantom) for opening and closing hinged sealing member 2, a fluid communication port 9, and a port for delivery of a scope 10 which may extend partially internally and partially externally of body 1. Here, the moveable rod comprises two sections, a section 3a internal to body 1 and an external section 3b which is coupled to section 3a by means of a multidirectional U-joint 26. U-joint 26 allows external section 3b to be freely rotated and pivoted with respect to internal section 3a while also controlling the position (opening and closing) of sealing member 2. A knob 27 mounted at the proximal end of section 3b provides easy manipulation, positioning, and locking of the rod sections. The passage of the rod 3a, fluid lumen 9, and light and scope 10 through the thickened section 25a permit opening and closing of sealing member 2, with and without upper section 23 attached to body 1. This design provides smooth surfaces on the outside of body 1 to provide atraumatic passage through and sealing against tissue, and on the inside of body 1 to provide an uncluttered surgical field and to seal upper section 23.

A handle 11 is mounted at the proximal end of body 1 or, when upper section 23 is in place, at the midsection of the combined structure. A lever arm 28 extends between handle 11 and a rotatable collar 24 which resides around the proximal end of body 1 and has tabbed ends 24a and 24b. Collar 24 is rotatable about the circumference of body 1 to position handle 11 for optimal access and working space for a surgeon. Lever arm 28 is connected to collar 24 at a joint 29 and to handle 11 by a moveable joint 30 which allow for further adjustment of the position of handle 11. The position of collar 24 about body 1, the position of lever arm 28 with respect to collar 24, and the position of handle 11 with respect to lever arm 28 are all adjustable and locked in place by means of a wing nut 31 at moveable joint 30. This three-way locking action is accomplished by the configuration of lever arm 28.

Figure 14:
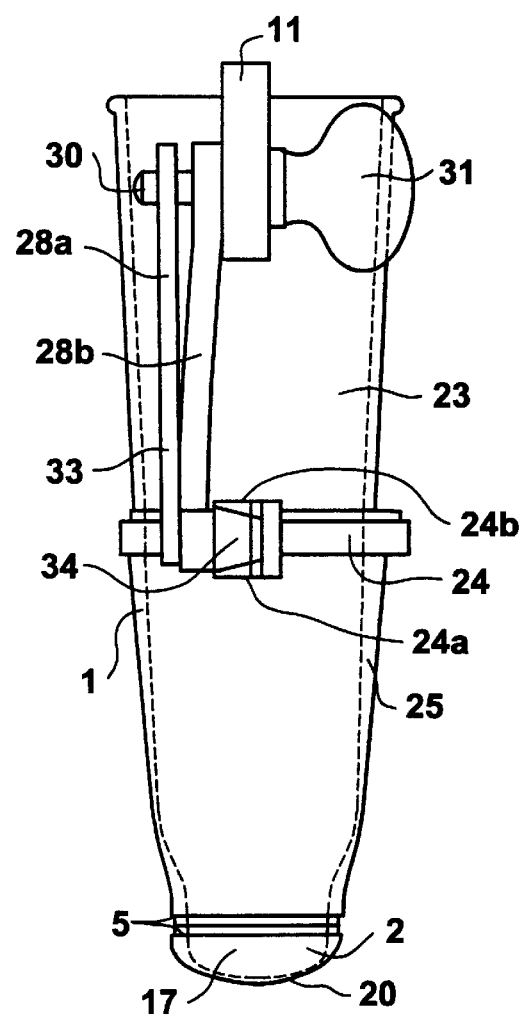
FIG. 14 is a cross-section of the embodiment of FIG. 13 through line 14—14 showing more detail of the handle mechanism.

As shown in FIG. 14, which is a view of the instrument of FIG. 13 along the line 14—14, lever arm 28 comprises two elongated lengths 28a and 28b, 28a having a threaded bore at its proximal end. The distal ends of lengths 28a and 28b are held together by threaded nut and bolt 32 (see FIG. 15), while the proximal ends are spaced apart. Thumbscrew 31 passes through the distal end of handle 11 and length 28b such that when thumbscrew 31 is rotated, length 28a is caused to compress against length 28b and handle 11, and thus, tighten joints 29 and 30. Upon this action, the distal ends of lengths 28a and 28b are caused to pivot away from each other about a fulcrum point 33. Extending from the distal end of length 28b is a tapered section 34 positioned within tabbed end 24b of collar 24, such that tabbed end 24b is caused to become wedged within tabbed end 24b and compress against tabbed end 24a when thumbscrew 31 is rotated, thereby tightening collar 24 around body 1 and locking handle 11 in a fixed position relative to body 1. With such a configuration, multiple orientations of handle 11 may be achieved, thus optimizing viewing and access of the targeted surgical area. Although a single-step three-way locking mechanism has been described, it will be appreciated by those skilled in the art that other handle adjustment and locking mechanisms and configurations may be employed with the present invention.

Figure 17:
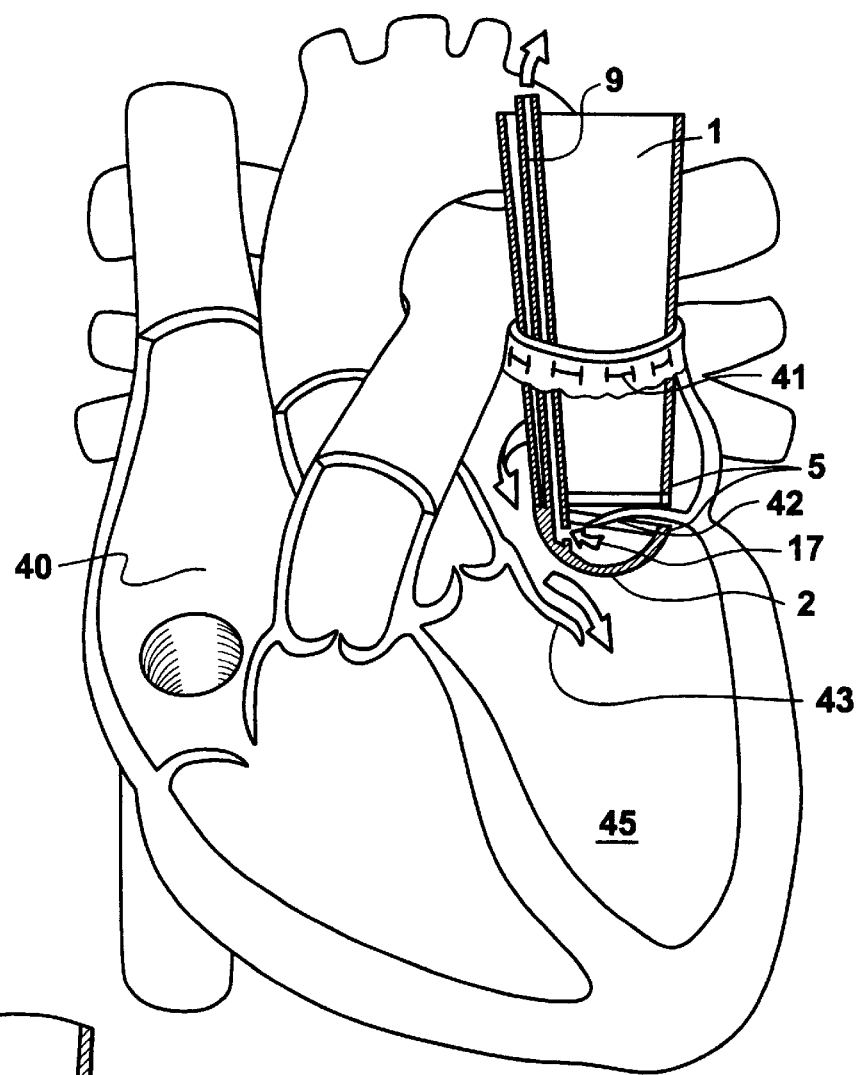
FIG. 17 is a schematic view of a heart having the body portion of an embodiment of the invention operably positioned within the mitral valve.

FIG. 17 is a schematic representation of a cross-section of the distal portion of an embodiment of the present invention operably positioned within the mitral valve of a beating heart 40. An incision is provided in the pericardial and myocardial layers of the heart 40 which has been temporarily sealed about the body 1 of the instrument with a purse-string suture 41 to prevent excess blood loss. One leaflet 42 of the mitral valve is positioned through the sealable opening and within the segregated surgical field. Conformable sealing member 5 creates a seal between the leaflet and the edge of body 1 and sealing member 2. Blood entering the surgical field 27 can be aspirated via fluid communication tube 9 which passes the blood to outside the patient's body. Together the sealing and fluid aspiration functions of the present invention act to provide a substantially bloodless segregated surgical field and to substantially stabilize valve leaflet 42. Surgical devices, such as scalpels, forceps, etc., may be introduced into the interior of body 1 to perform the necessary surgical repair. As the surgery is performed, the heart remains beating and the valve's other leaflet 43 continues its normal function to maintain blood flow through the space between sealing member 2 and valve leaflet 43 to the left ventricle 45 of heart 40.

Figure 18:
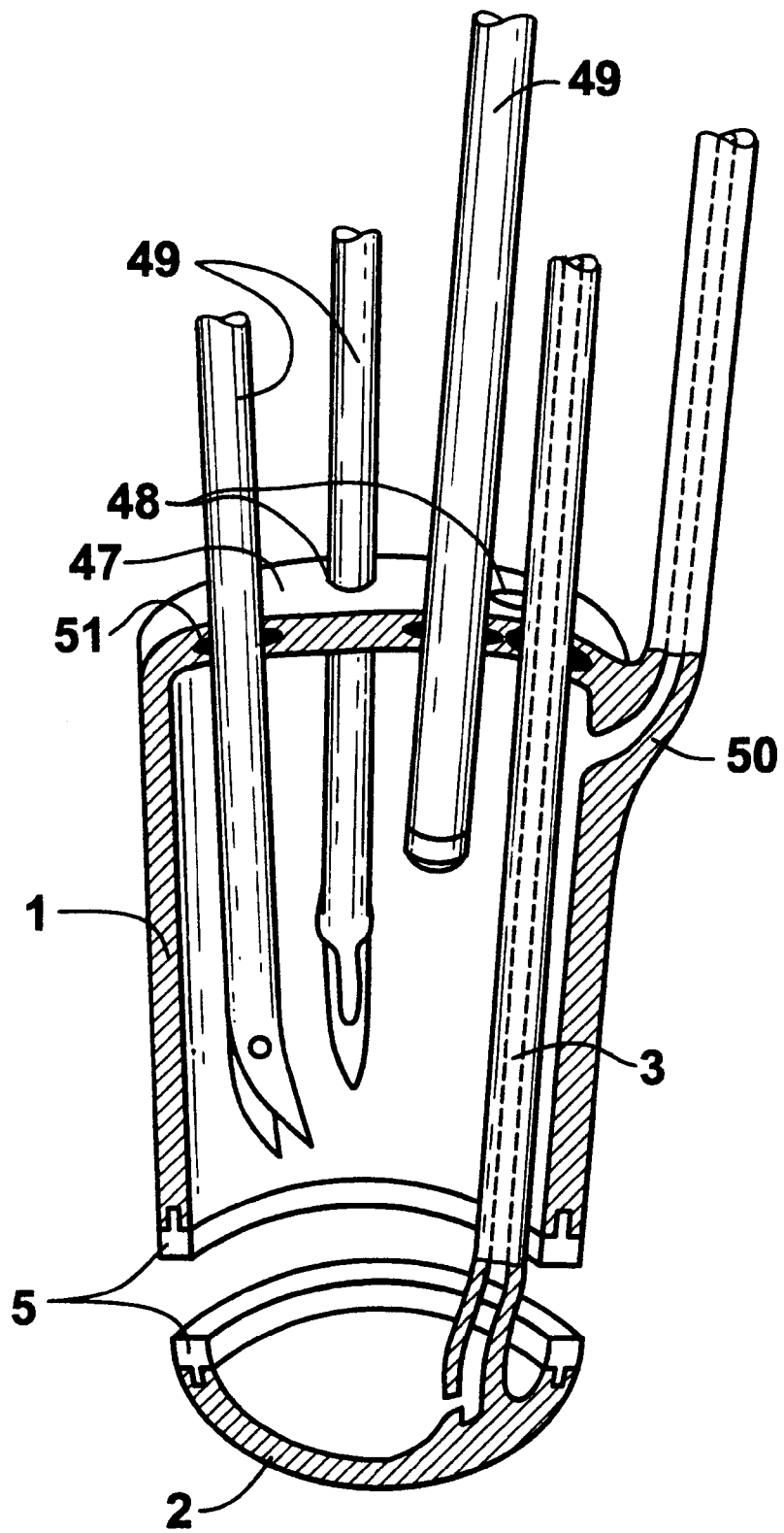
FIG. 18 is cross-section of another embodiment of the present invention having a covered top portion with sealable tool ports.

Another embodiment of the present invention is illustrated in FIG. 18 which obviates the need for an extended internal volume. Here, the body 1 has a covered proximal end 47 which prevents the overflow of blood. Multiple ports 48 are provided, however, through covered surface 47 for delivering surgical tools 49 (e.g., scalpel, scissors, scope, etc.) and the like to the surgical field. Each of tool delivery ports 48 is sealed closed when not occupied with a tool by means of a rubber seal 51. Seal 51 further acts to seal a tool 49 within a port 48 to prevent seepage of blood. The configuration of sealing member 2 and movable rod 3 are similar to that of FIG. 12, however, a fluid communication port 9 is integral with rod 3 to evacuate the blood. A venting port 50 is provided so as to equalize the pressure within body 1 when aspiration is taking place. Alternately, port 50 may be used for fluid delivery or injection, for example, to deliver a saline solution to provide a clear viewing space within body 1.

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims.

What is claimed is:

1. An instrument for performing surgery on a heart comprising:

an elongate body having a proximal end having a proximal opening, a distal end having a distal opening, and a substantially unobstructed central interior region extending from said distal opening to said proximal opening;

a sealing member on the distal end of the elongate body for opening and closing the distal opening when the sealing member disengages and engages, respectively, the distal end of the elongate body;

a conformable seal of compressible material to conform to a portion of the heart and located on at least one of the distal end of the elongate body and an upper surface of the sealing member, said conformable seal providing a fluid impermeable seal between the distal end of the elongate body and the sealing member; and an actuator positioned so as not to substantially obstruct said unobstructed central interior region, said actuator for selectively moving the sealing member into engagement with the distal end of the elongate body, thereby providing a segregated surgical field within the unobstructed central interior region of the elongate body into which a surgical tool may be introduced.

2. The instrument of claim 1, further comprising a locking mechanism for securing the sealing member in engagement with the distal end of the elongate body.

3. The instrument of claim 1, further comprising a cover associated with said proximal opening, said cover having at least one sealable port for directing a surgical tool into the segregated surgical field.

4. The instrument of claim 1, further comprising an aspiration tube extending between the proximal and distal ends of the elongate body, the aspiration tube having an inlet adjacent the segregated surgical field within the unobstructed central interior region.

5. The instrument of claim 1, wherein the elongate body is substantially cylindrical.

6. The instrument of claim 1 wherein said actuator is affixed to said sealing member.

7. The instrument of claim 1 further comprising a housing mounted to the exterior of said elongate body, wherein said actuator comprises a moveable rod contained within said housing.

8. An instrument for performing surgery on a heart, comprising:

an elongate body having a proximal end, a distal end, an substantially unobstructed central interior region extending from said proximal end to said distal end defining a surgical field, and a distal opening in the distal end communicating with the interior region;

a sealing member operably associated with the distal end of the elongate body for providing a sealable distal opening between the elongate body and the sealing member; at least one of said elongate body distal end and said sealing member including a portion of compressible material so as to conform to a portion of the heart during use, and means for actuating the sealing member against the distal end of the elongate body, thereby substantially segregating the surgical field within the interior region of the elongate body from a region surrounding the distal end of the elongate body, said means for actuating the sealing member being positioned so as not to obstruct said central interior region.

9. The instrument of claim 8, wherein the compressible material compresses a conformable seal between the sealing member and the distal end of the elongate body.

10. The instrument of claim 8, wherein the means for actuating the sealing member comprises a locking mechanism for substantially securing the sealing member against the distal end of the elongate body.

11. The instrument of claim 8, wherein the means for actuating the sealing member is attached to the elongate body.

12. An instrument for creating a segregated surgical field for operating on a target site within a heart, comprising:

an instrument body having a proximal opening, a distal opening and a substantially unobstructed interior extending therebetween;

a sealing member at the distal end of the instrument body, said sealing member having an open position relative to said instrument body for receiving a portion of the heart into said interior and a substantially closed position against said instrument body at least one of said instrument distal opening and said seal member including a portion made of compressible material so as to seal and around said portion of the heart when said sealing member is in said closed position thereby segregating said portion of the heart received into said interior means for positioning the sealing member to said closed position.

13. The instrument of claim 12, wherein said compressible material comprises a conformable seal attached to said sealing member, said conformable seal adapted to engage at least a portion of said instrument body when said sealing member is in said closed position.

14. The instrument of claim 13, further comprising a means for positioning the sealing member.

15. The instrument of claim 12, wherein said means for positioning the sealing member is located exterior of said interior of said instrument body.

16. The instrument of claim 12, wherein said means for positioning the sealing member is positioned within said interior and in close proximity to the periphery of said interior.

17. The instrument of claim 12, further comprising a fluid communication tube extending from said segregated surgical field within said interior to a location outside said instrument body.

18. The instrument of claim 17, further comprising a handle extending from said proximal end of said instrument body.

19. The instrument of claim 12, wherein said proximal opening is larger than said distal opening.

20. The instrument of claim 12, wherein said sealing member is substantially concave with respect to said instrument body.

21. The instrument of claim 20, further comprising a fluid communication tube extending from a location within said concave sealing member to a location outside said instrument body.

22. The instrument of claim 12, wherein said compressible material comprises a conformable seal about said distal opening, said conformable seal adapted to engage at least a portion of said sealing member when said sealing member is in said closed position.

23. The instrument of claim 12, wherein said compressible material comprises a first conformable seal attached thereto and said instrument body further comprises a second conformable seal about said distal opening, said first conformable seal adapted to engage at least a portion of said second conformable seal when said sealing member is in said closed position.

24. The instrument of claim 23, wherein said first conformable seal and said second conformable seal are annular.

25. The instrument of claim 23, wherein said first sealing member and said second sealing member are made from a highly compressible material so as to conform around said portion of the heart received into said interior thereby maintaining said seal between said sealing member and said instrument body.

26. The instrument of claim 25, wherein said highly compressible material is an elastomer.

27. The instrument of claim 26, wherein said highly compressible material is silicone.

28. The instrument of claim 12, wherein said instrument body is substantially conical shaped, having a diameter which narrows proximally to distally.

29. The instrument of claim 28, wherein said instrument body has an external diameter at said proximal end of about 1.6 inches.

30. The instrument of claim 28, wherein said instrument body has an external diameter at said distal end of about 1.2 inches.

31. The instrument of claim 12, further comprising a means for locking said sealing member in said closed position.

32. The instrument of claim 1 wherein said unobstructed central interior region has a diameter of about 1.0 inch.

* * * * *